US010987255B2

(12) United States Patent
Ohtsubo

(10) Patent No.: US 10,987,255 B2
(45) Date of Patent: Apr. 27, 2021

(54) STRETCHABLE AND CONTRACTIBLE SHEET AND ABSORBENT ARTICLE

(71) Applicant: UNICHARM Corporation, Ehime (JP)

(72) Inventor: Toshifumi Ohtsubo, Kagawa (JP)

(73) Assignee: UNICHARM Corporation, Ehime (JP)

( * ) Notice: Subject to any disclaimer, the term of this patent is extended or adjusted under 35 U.S.C. 154(b) by 0 days.

(21) Appl. No.: 16/752,333

(22) Filed: Jan. 24, 2020

(65) Prior Publication Data

US 2020/0155371 A1    May 21, 2020

Related U.S. Application Data

(63) Continuation of application No. PCT/JP2018/036256, filed on Sep. 28, 2018.

(30) Foreign Application Priority Data

Oct. 4, 2017   (JP) .............................. JP2017-194554

(51) Int. Cl.
*A61F 13/15*     (2006.01)
*A61F 13/49*     (2006.01)
(Continued)

(52) U.S. Cl.
CPC .. *A61F 13/49019* (2013.01); *A61F 13/49014* (2013.01); *B32B 5/022* (2013.01);
(Continued)

(58) Field of Classification Search
CPC .......... A61F 13/49019; A61F 13/49014; A61F 13/496; A61F 13/51; A61F 2013/49093;
(Continued)

(56) References Cited

U.S. PATENT DOCUMENTS 5,626,574 A * 5/1997 Sasaki ................. B29C 66/1122
604/385.29
2006/0270302 A1    11/2006 Ando et al.
(Continued)

FOREIGN PATENT DOCUMENTS

CN    102525744 A    7/2012
CN    204909840 U    12/2015
(Continued)

OTHER PUBLICATIONS

International Search Report issued in corresponding International Application No. PCT/JP2018/036256, dated Nov. 13, 2018, with translation (5 pages).
(Continued)

*Primary Examiner* — Jacqueline F Stephens
(74) *Attorney, Agent, or Firm* — Osha Bergman Watanabe & Burton LLP

(57) ABSTRACT

A stretchable/contractible sheet having an up-down direction and a left-right direction intersecting each other includes a first sheet; a second sheet; welded portions; and elastic members. Elastic members are arranged between the first sheet and the second sheet by welded portions and with a space in the up-down direction. The welded portions include a first welded portion; and a third welded portion. The welded portions further include a second welded portion; and a fourth welded portion. The first welded portion and the third welded portion have portions that overlap in the up-down direction. A length of a portion where the first welded portion and the third welded portion overlap in the up-down direction is larger than a length in the up-down direction between a lowermost end of the first welded portion and a lowermost end of the third welded portion.

18 Claims, 8 Drawing Sheets

(51) Int. Cl.
  *B32B 7/05* (2019.01)
  *B32B 5/02* (2006.01)
  *B32B 27/12* (2006.01)
  *B32B 27/32* (2006.01)
  *A61F 13/496* (2006.01)

(52) U.S. Cl.
  CPC ............... *B32B 7/05* (2019.01); *B32B 27/12* (2013.01); *B32B 27/32* (2013.01); *A61F 13/496* (2013.01); *A61F 2013/49093* (2013.01); *B32B 2307/51* (2013.01); *B32B 2307/726* (2013.01); *B32B 2555/02* (2013.01)

(58) Field of Classification Search
  CPC ........ B32B 5/022; B32B 27/32; D04H 1/559; D04H 1/74
  See application file for complete search history.

(56) References Cited

U.S. PATENT DOCUMENTS

| | | | |
|---|---|---|---|
| 2016/0058624 A1 | 3/2016 | Hohm et al. | |
| 2016/0058627 A1* | 3/2016 | Barnes ................ | A61F 13/5655 604/385.3 |
| 2017/0049639 A1* | 2/2017 | Shimazu ........... | A61F 13/49058 |

FOREIGN PATENT DOCUMENTS

| | | |
|---|---|---|
| CN | 105455954 A | 4/2016 |
| CN | 205586162 U | 9/2016 |
| CN | 106163477 A | 11/2016 |
| JP | 2001-504899 A | 4/2001 |
| JP | 2008-154998 A | 7/2008 |
| JP | 2012-217553 A | 11/2012 |
| JP | 2015160102 A | 9/2015 |
| JP | 6171120 B1 | 7/2017 |
| WO | 2016160752 A1 | 10/2016 |

OTHER PUBLICATIONS

Written Opinion issued in corresponding International Application No. PCT/JP2018/036256, dated Nov. 13, 2018 (5 pages).
International Preliminary Report on Patentability issued in corresponding International Application No. PCT/JP2018/036256, dated Apr. 8, 2020, with translation (10 pages).
Extended European Search Report issued in the counterpart European Patent Application No. 18864476.9, dated Oct. 30, 2020 (8 pages).
Office Action issued in the counterpart Chinese Patent Application No. 201880057438.X, dated Aug. 31, 2020 (14 pages).
Examination Report issued in corresponding GCC Application No. GC2018-36154 dated Feb. 1, 2021 (7 pages).

* cited by examiner

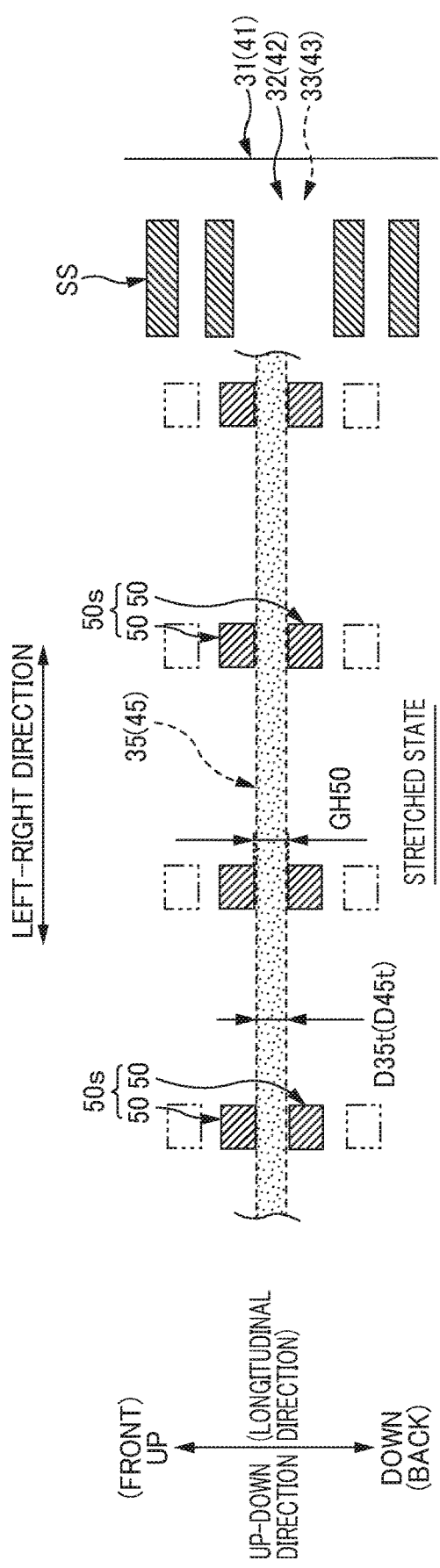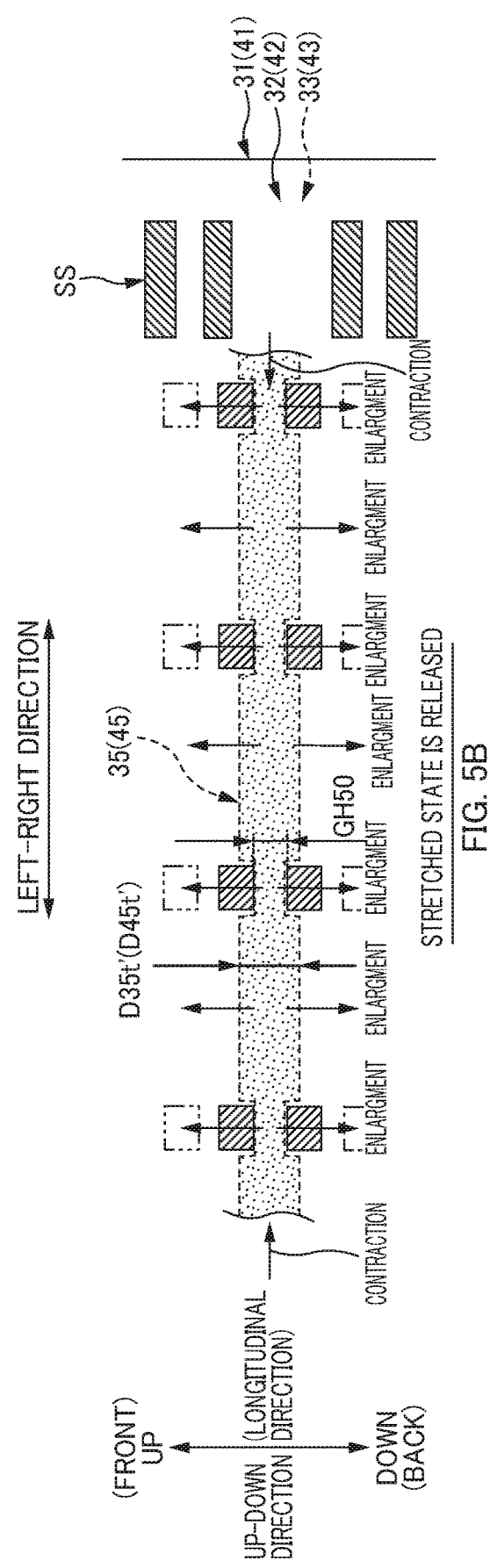

STRETCHABLE AND CONTRACTIBLE SHEET AND ABSORBENT ARTICLE

CROSS-REFERENCE TO RELATED APPLICATIONS

This application is based on and claims priority under 35 U.S.C. § 119 from Japanese Patent Application No. 2017-194554 filed on Oct. 4, 2017, the contents of which are incorporated herein by reference.

TECHNICAL FIELD

The present invention generally relates to a stretchable/contractible sheet and an absorbent article.

BACKGROUND

As an example of an absorbent article that absorbs excrement such as urine, a disposable diaper is known. As a waist member of a disposable diaper, a sheet member is generally employed to which stretch/contraction ability is applied by attaching elastic members thereto with adhesive such as hot-melt adhesive. But, in the case where the elastic members are attached with adhesive, curing of the adhesive attached onto the outer surface of elastic members causes a risk of deterioration of elasticity of the elastic members, that is stretch/contraction ability, and/or causes a risk of deterioration of flexibility of the sheet member. Therefore, attaching elastic members to a sheet member without adhesive is recently considered.

For example, wire-like elements being capable of elastically stretching are arranged between two sheet members stacked in the thickness direction while being stretched in the lengthwise direction. And, the two sheet members are joined with a plurality of joints which are formed by means such as welding means. When the wire-like elements are released from their stretched state and contract in the lengthwise direction so that their outer diameter are thicker, each wire-like element is sandwiched by a pair of joints arranged on both sides in the radial direction of the wire-like element, fixing the wire-like elements between the sheet members. There is disclosed such a technique for manufacturing a sheet member having a stretch/contraction ability without adhesive, which is applied to an absorbent article such as a napkin or a diaper (see PTL 1).

CITATION LIST

Patent Literature

[PTL 1] Japanese Unexamined Patent Application Publication (Translation of PCT Application) No. 2001-504899

In a stretchable/contractible sheet member of PTL 1, when wire-like elements are stretched at the time of using a diaper, the outer diameters (the diameters) of the wire-like elements become smaller; there is a risk that the wire-like elements are displaced from between each pair of joints arranged on both radial sides of each wire-like element. The wire-like elements repeat stretching and contracting, and as a result, the positions where the wire-like elements are fixed are displaced. This makes it difficult to exert even and uniform contraction force on sheet members.

SUMMARY

One or more embodiments provide a stretchable/contractible sheet having flexibility and in which displacement of the elastic members is less likely to happen.

One or more embodiments provide a stretchable/contractible sheet having an up-down direction and a left-right direction intersecting each other. The stretchable/contractible sheet includes:
a first sheet;
a second sheet;
a plurality of welded portions joining the first sheet and the second sheet; and
a plurality of elastic members being capable of stretching/contracting in the left-right direction,
the plurality of elastic members arranged between the first sheet and the second sheet by the plurality of welded portions and with a space in the up-down direction,
the plurality of welded portions including, above a certain elastic member of the plurality of the elastic members,
a first welded portion and
a third welded portion adjacent to the first welded portion on a one side in the left-right direction,
the plurality of welded portions further including, below the certain elastic member,
a second welded portion and
a fourth welded portion adjacent to the second welded portion on the one side,
the certain elastic member attached to the first sheet and the second sheet
by being sandwiched in the up-down direction between the first welded portion and the second welded portion while contracting in the left-right direction, and
by being sandwiched in the up-down direction between the third welded portion and the fourth welded portion,
the first welded portion and the third welded portion having portions overlapping in the up-down direction,
a position of a lower end of the first welded portion being different in the up-down direction from a position of a lower end of the third welded portion.

Other features of one or more embodiments will become apparent from the description in this specification and the attached drawings.

According to one or more embodiments, it is possible to provide a stretchable/contractible sheet having flexibility and in which displacement of the elastic members is less likely to happen.

BRIEF DESCRIPTION OF DRAWINGS

FIGS. 5A and 5B are diagrams showing a function to attach an elastic member 35, and are magnified view of the portion C in FIG. 4.

DETAILED DESCRIPTION

Figure 1:
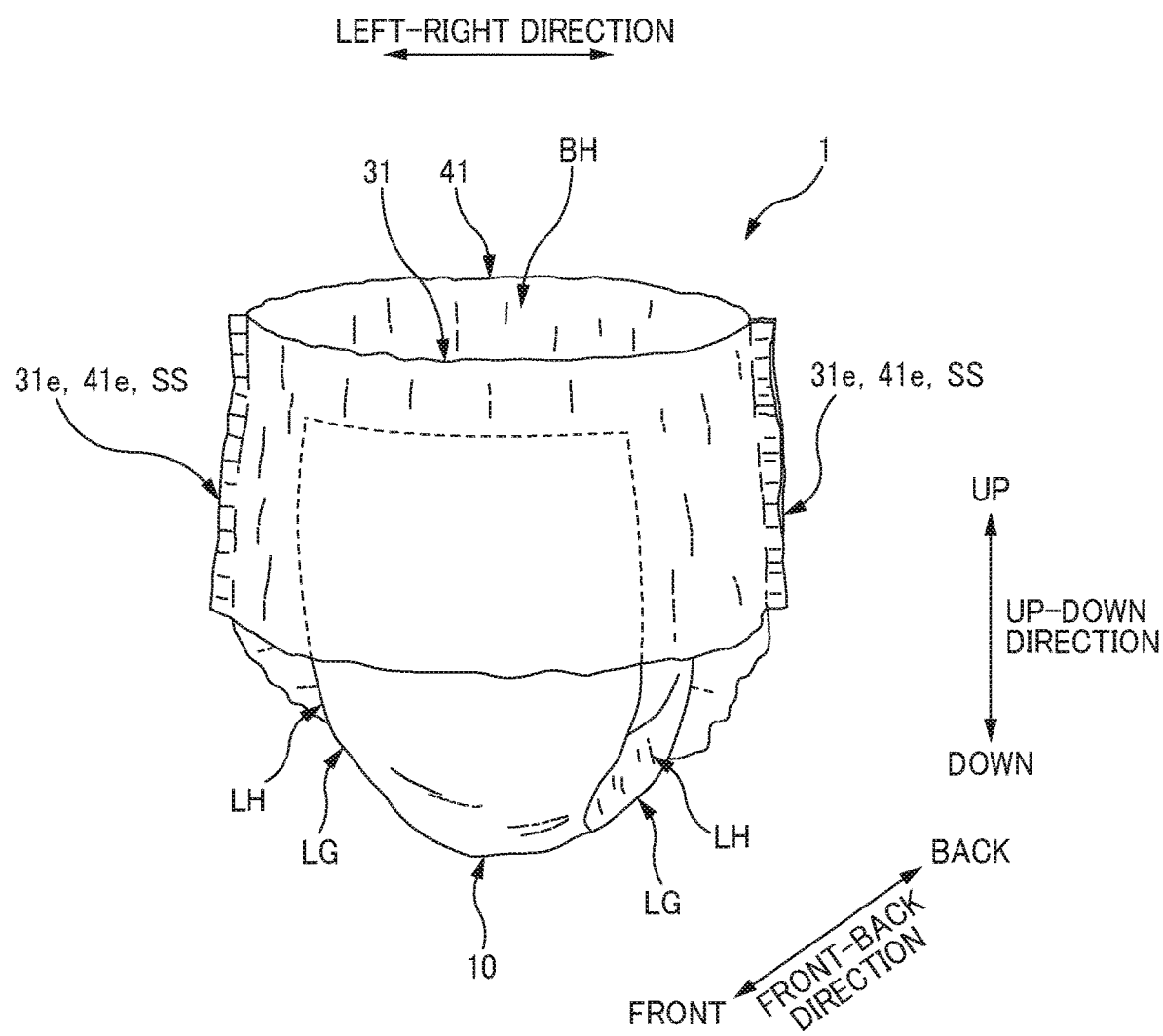
FIG. 1 is a schematic perspective view of a diaper 1.

At least the following matters will be made clear by the description in the present specification and the accompanying drawings.

A stretchable/contractible sheet has an up-down direction and a left-right direction intersecting each other. The stretchable/contractible sheet, includes:
a first sheet;
a second sheet;
a plurality of welded portions joining the first sheet and the second sheet; and
a plurality of elastic members being capable of stretching/contracting in the left-right direction,
  the plurality of elastic members arranged between the first sheet and the second sheet by the plurality of welded portions and with a space in the up-down direction,
  the plurality of welded portions including, above a certain elastic member of the plurality of the elastic members,
    a first welded portion and
    a third welded portion adjacent to the first welded portion on a one side in the left-right direction,
  the plurality of welded portions further including, below the certain elastic member,
    a second welded portion and
    a fourth welded portion adjacent to the second welded portion on the one side,
  the certain elastic member attached to the first sheet and the second sheet
    by being sandwiched in the up-down direction between the first welded portion and the second welded portion while contracting in the left-right direction, and
    by being sandwiched in the up-down direction between the third welded portion and the fourth welded portion,
  the first welded portion and the third welded portion having portions overlapping in the up-down direction,
  a position of a lower end of the first welded portion being different in the up-down direction from a position of a lower end of the third welded portion.

With such a stretchable/contractible sheet, in the up-down direction, the space between the third welded portion and the second welded portion is smaller than the space between the first welded portion and the second welded portion. Accordingly, even if the outer diameter of the elastic member becomes smaller when being stretched in the left-right direction from the natural state, the lower end of the third welded portion and the upper end of the second welded portion exerts friction force on the elastic member, making it possible to suppress displacement of the elastic member in the left-right direction. Since the elastic member is not joined by means such as adhesive, it is possible to realize a stretchable/contractible sheet having flexibility and in which displacement of the elastic members is less likely to happen.

In such a stretchable/contractible sheet, a length of a portion where the first welded portion and the third welded portion overlap in the up-down direction is larger than a length in the up-down direction between a lowermost end of the first welded portion and a lowermost end of the third welded portion.

With such a stretchable/contractible sheet, the up-down-direction displacement of two welded portions adjacent in the left-right direction is restricted to a predetermined range. This suppresses attaching of the elastic member with being inclined according to the displacement of the welded portions. This prevents stretching/contracting force of the elastic member from being exerted in the up-down direction. This makes it easier to suppress deterioration of fit around the waist part of the absorbent article.

In such a stretchable/contractible sheet, an outer diameter of the elastic member when the elastic member is stretched to a maximum stretchable length in the left-right direction is larger than a length in the up-down direction between a lowermost end of the first welded portion and a lowermost end of the third welded portion.

With such a stretchable/contractible sheet, when arranging the elastic member between the welded portions, the inclination of the elastic member in the up-down direction becomes relatively large. This suppresses the curving and meandering of the elastic member. This prevents stretching/contracting force of the elastic member from being exerted in the up-down direction. This makes it easier to suppress deterioration of fit around the waist part of the absorbent article.

In such a stretchable/contractible sheet, a length of the first welded portion in the left-right direction is larger than a length of the first welded portion in the up-down direction.

With such a stretchable/contractible sheet, since the shape of the welded portion is laterally elongated, this increases the area (length) of a portion in which the elastic member and the welded portion are in contact with each other in the left-right-direction. Accordingly, friction force produced in the contact portion can increase. This makes it difficult to cause displacement of the elastic members fixed by the welded portions, and the stretchable/contractible sheet can have a reliable stretch/contraction ability.

In such a stretchable/contractible sheet, the second welded portion and the third welded portion have a shape in which four corners of a rectangle are cut out.

With such a stretchable/contractible sheet, the four corners of the welded portion have cut-outs, and this elongates the length of a portion where the elastic member and the welded portion are in contact with each other, producing a larger friction force. This makes it possible to suppress displacement of the elastic members.

In such a stretchable/contractible sheet, the second welded portion and the third welded portion have an elliptical shape.

With such a stretchable/contractible sheet, the elastic member is in contact along curved (elliptical) lines of the welded portion. This makes longer the length along which the elastic member can be in contact with the welded portion, producing a larger friction force. This makes it possible to suppress displacement of the elastic members.

In such a stretchable/contractible sheet, the first to the fourth welded portions have an identical shape.

With such a stretchable/contractible sheet, when forming the welded portions by means such as an ultrasonic welding device, it is possible to simplify the configuration of such a device. This reduces production cost, and makes easier maintenance of the device.

In such a stretchable/contractible sheet, an outer diameter of the elastic member when the elastic member is stretched to a maximum stretchable length in the left-right direction is smaller than a length in the up-down direction between a lowermost end of the first welded portion and an uppermost end of the second welded portion, and that the outer diameter of the elastic member when the elastic member is stretched to the maximum stretchable length in the left-right direction is smaller than a length in the up-down direction between a lowermost end of the third welded portion and an uppermost end of the fourth welded portion.

With such a stretchable/contractible sheet, it can be easy to arrange the elastic member between a welded portion pair adjacent in the up-down direction. That is, it is possible to form the welded portion pair without overlapping the elastic member. This makes it possible to prevent cut of the elastic member, which is caused by applying ultrasonic vibration onto the elastic member in the production processes.

In such a stretchable/contractible sheet, an outer diameter of the elastic member when the elastic member is stretched to a maximum stretchable length in the left-right direction is smaller than
    a length in the up-down direction between a lowermost end of the third welded portion and an uppermost end of the second welded portion.

With such a stretchable/contractible sheet, it is possible to arrange the elastic member in a space smaller than the space between a welded portion pair adjacent in the up-down direction. That is, it is possible to form the welded portion pair with overlapping neither of the third welded portion nor the second welded portion. This makes it easier to prevent the elastic member from being cut in the production processes.

In such a stretchable/contractible sheet, the plurality of welded portions including, above the certain elastic member, a fifth welded portion adjacent to the third welded portion on the one side, and
    that an outer diameter of the elastic member when the elastic member is stretched to a maximum stretchable length in the left-right direction
    is smaller than
    a length in the up-down direction between a lowermost end of the fifth welded portion and an uppermost end of the second welded portion.

With such a stretchable/contractible sheet, it is possible to arrange the elastic member in a space between the fifth welded portion and the second welded portion, which is smaller than an up-down-direction space between the third welded portion and the second welded portion. This makes it easier to prevent the elastic member from being cut in the production processes.

In such a stretchable/contractible sheet, a length in the up-down direction between a lowermost end of the first welded portion and an uppermost end of the second welded portion
    is equal to
    a length in the up-down direction between a lowermost end of the third welded portion and an uppermost end of the fourth welded portion.

With such a stretchable/contractible sheet, the welded-portion row composed of the welded portions that are uniformly arranged is formed. This suppresses breakage of a portion of the front band member (the back band member) having a locally small strength of joining the first sheet and the second sheet, and also suppresses deterioration of touch of a portion having locally large strength of joining.

In such a stretchable/contractible sheet, an outer diameter of the elastic member when the elastic member is stretched to 70% of a maximum stretchable length in the left-right direction
    is larger than
    a length in the up-down direction between a lowermost end of the third welded portion and an uppermost end of the second welded portion.

With such a stretchable/contractible sheet, in a usual use of the absorbent article, the outer diameter of the elastic member is always larger than the up-down-direction space between the lowermost end of the third welded portion and the uppermost end of the second welded portion. This makes it possible for the third welded portion and the second welded portion to more reliably suppress displacement of the elastic members.

In such a stretchable/contractible sheet, in the left-right direction, a space of two adjacent welded portions is less than or equal to 6 mm.

With such a stretchable/contractible sheet, the space of two welded portions adjacent in the left-right direction is small, and this makes it easier to produce effective friction force between the two welded portions and the elastic member. This makes it easier to suppress left-right-direction displacement of the elastic members.

An absorbent article has an up-down direction and a left-right direction intersecting each other. The absorbent article includes:
    an absorbent main body that absorbs excrement;
    a front band member provided along the left-right direction and joined to a front-upper-end portion of the absorbent main body; and
    a back band member provided along the left-right direction separately from the front band member, and joined to a back-upper-end portion of the absorbent main body,
    the front band member and the back band member including:
        a first sheet;
        a second sheet; and
        a plurality of welded portions joining the first sheet and the second sheet,
        a plurality of elastic members being capable of stretching/contracting in the left-right direction,
        the plurality of elastic members arranged with a space in the up-down direction and between the first sheet and the second sheet,
        the plurality of welded portions including, above a certain elastic member of the plurality of elastic members,
        a first welded portion and
        a third welded portion adjacent to the first welded portion on a one side in the left-right direction,
        the plurality of welded portions further including, below the certain elastic member,
        a second welded portion and
        a fourth welded portion adjacent to the second welded portion on the one side,
        the certain elastic member attached to the first sheet and the second sheet
            by being sandwiched in the up-down direction between the first welded portion and the second welded portion while contracting in the left-right direction, and
            by being sandwiched in the up-down direction between the third welded portion and the fourth welded portion,
        the first welded portion and the third welded portion having portions overlapping in the up-down direction, a position of a lower end of the first welded portion being different in the up-down direction from a position of a lower end of the third welded portion.

With such an absorbent article, in the front band member (the back band member) that is in contact with the wearer's waist, it is difficult for displacement of the elastic member to occur. This suppresses local concentration of stretching/contracting force of the elastic member, and also suppresses deterioration of exertion of the stretching/contracting force. This makes it possible to keep good fit around the waist part of a wearer.

In such an absorbent article, in the up-down direction, a space of the elastic members disposed in the front band member is different from a space of the elastic members disposed in the back band member.

With such an absorbent article, the size and the shape of creases formed on each surface can be different between the front band member and the back band member. Accordingly, the front band member and the back band member are less likely to be in close contact in the thickness direction. This can make it easier to open the front band member and the back band member in the front-back direction to form a waist opening when putting on the absorbent article.

In such an absorbent article, in the up-down direction, a space of the elastic members disposed in the front band member is smaller than a space of the elastic members disposed in the back band member.

With such an absorbent article, in the back band member in which the pitch between the elastic members in the up-down direction is large, it can be easier to form large creases. Accordingly, in the region of buttocks whose movement is large, the back band member becomes more likely to stretch following the wearer's body movement, improving fit.

<Configuration of Disposable Diaper>

Figure 2:
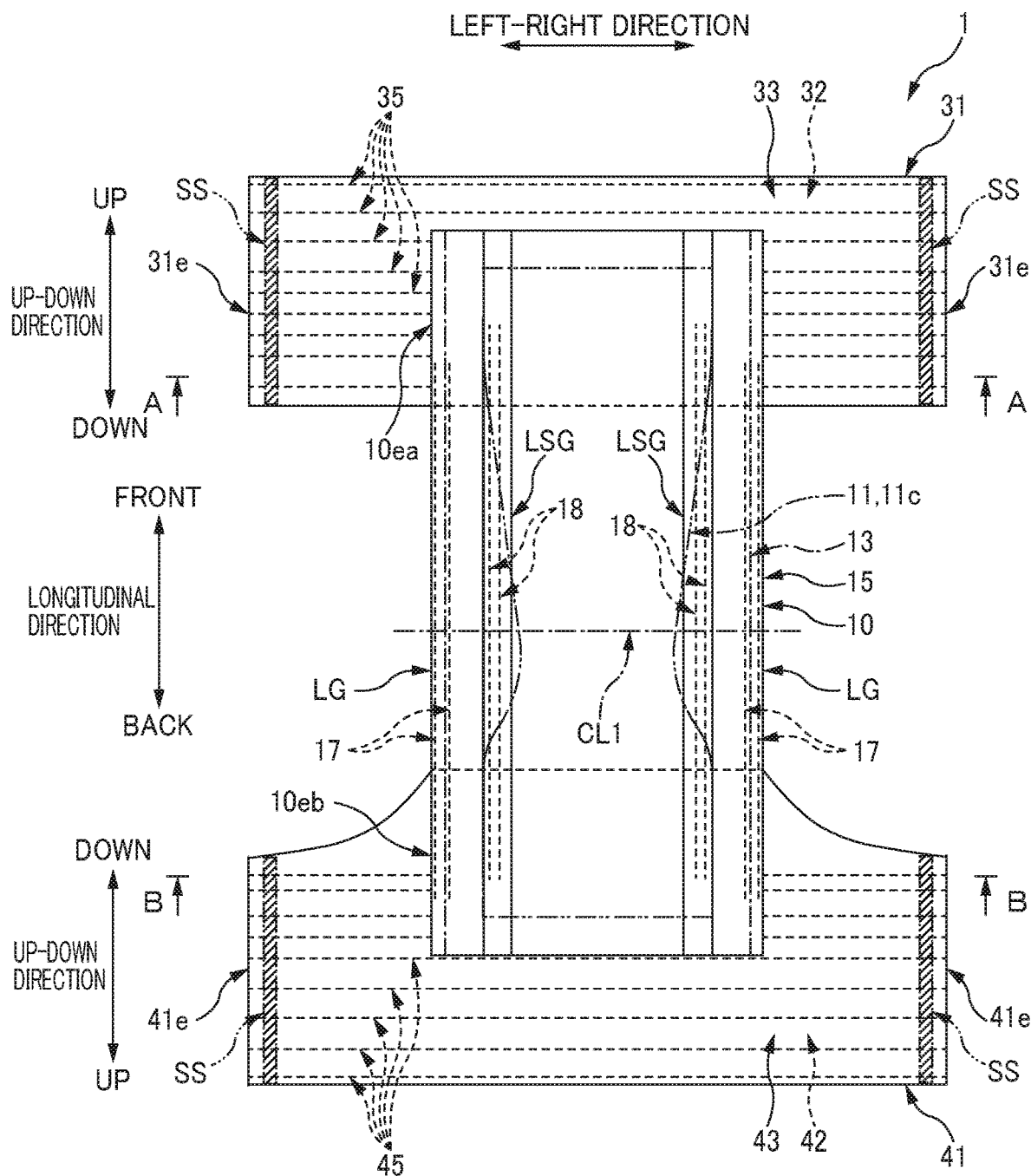
FIG. 2 is a schematic plan view of a diaper 1 which is opened and stretched, as viewed from the skin side of a wearer.
Figure 3:
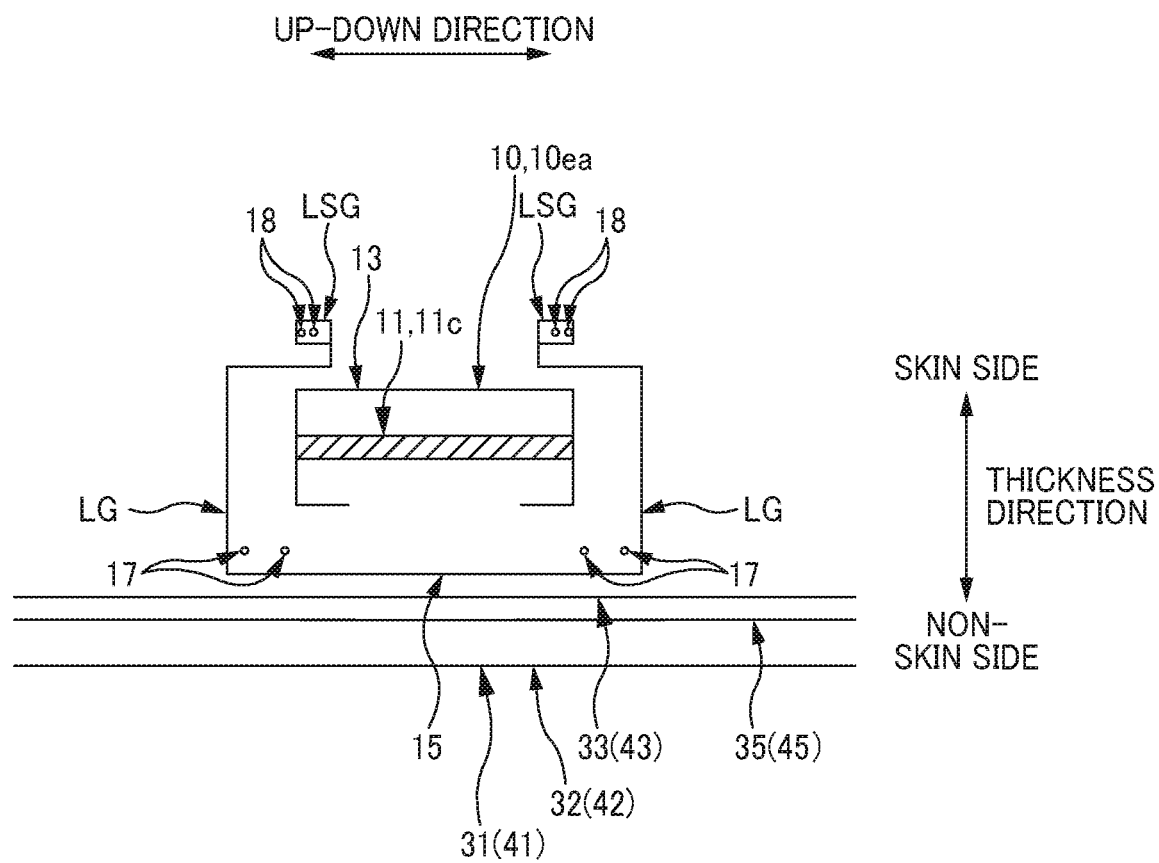
FIG. 3 is a diagram illustrating the configuration of an absorbent main body 10.

An absorbent article to which a stretchable/contractible sheet according to the present embodiment is applied is exemplified by a disposable diaper 1 (hereinafter referred to as a "diaper 1"), and it will be described below. In the diaper 1, a stretchable/contractible sheet is used as waist band members (a front band member 31 and a back band member 41; to be described later). FIG. 1 is a schematic perspective view of a diaper 1. FIG. 2 is a schematic plan view of the diaper 1 which is opened and stretched, as viewed from the skin side of a wearer. FIG. 3 is a cross-sectional view taken along line A-A in FIG. 2, and is also a cross-sectional view taken along line B-B in FIG. 2.

When the diaper 1 is in a state where it has a pants shape before being worn shown in FIG. 1, the diaper 1 has: an "up-down direction"; a "left-right direction" perpendicular to the up-down direction; and a "front-back direction" perpendicular to the up-down direction and the left-right direction. In the up-down direction, the upper side corresponds to the waist opening side for a wearer, and the lower side corresponds to the wearer's crotch side. In the front-back direction, the front side corresponds to the side of a wearer's front, and the back side corresponds to the side of a wearer's back.

When being in a pants shape shown in FIG. 1, the diaper 1 includes: a front band member 31 that has a stretch/contraction ability along the left-right direction; a back band member 41 which is located back the front band member 31 and which has a stretch/contraction ability along the left-right direction for forming a waist opening BH on the up side in the up-down direction in cooperation with the front band member 31; and an absorbent main body 10 disposed between the front band member 31 and the back band member 41 as a crotch portion. The absorbent main body 10 is located projecting downward in the up-down direction beyond the front band member 31 and the back band member 41.

In the left-right direction, the end portions 31e and 31e of the front band member 31 are joined with the corresponding end portions 41e and 41e of the back band member 41 by a side seal portion SS serving as a welded portion. Thus, the front band member 31 and the back band member 41 form, together with the absorbent main body 10, a leg opening LH on each side in the left-right direction and on the underside.

An "opened state" of the diaper 1 is a state in which the pants-shaped diaper 1 in FIG. 1 is opened on a plane by separating the front band member 31 and the back band member 41 by unjoining the joining of foregoing side seal portions SS on both sides in the left-right direction, and by opening the diaper 1 in the up-down direction. A "stretched state" is a state in which a product (the diaper 1) is stretched without creases, specifically, it is a state in which members constituting the diaper 1 (e.g., the absorbent main body 10 and the front band member 31) are stretched until the length of each member becomes substantially equal to its original length.

In the opened state, the diaper 1 has three directions perpendicular to one another: the longitudinal direction; the left-right direction; and the thickness direction (a direction penetrating the paper plane of FIG. 2). The longitudinal direction extends along the foregoing up-down direction. The one side of the longitudinal direction corresponds to the front side, and the other side corresponds to the back side. The outer side in the longitudinal direction corresponds to the up side in the up-down direction (the waist opening side), and the inner side in the longitudinal direction corresponds to the down side in the up-down direction (crotch side). Thus, since the longitudinal direction and the up-down direction are similar to each other, the following description related to the opened state will sometimes be made using the up-down direction instead of the longitudinal direction for the purpose of explanation. Meanwhile, the left-right direction in the opened state is identical to the left-right direction in the foregoing pants-shaped diaper. In the thickness direction, the one side corresponds to the skin side which is in contact with a wearer's body, and the other side corresponds to the non-skin side, which is opposite thereto. The thickness direction extends along the foregoing front-back direction.

In the opened state in FIG. 2, the front band member 31 is placed along the left-right direction, and the back band member 41 is placed along the left-right direction, with a certain longitudinal space from the front band member 31. The absorbent main body 10 is placed along the longitudinal direction between the front band member 31 and the back band member 41. And, the longitudinal end portions 10ea and 10eb of the absorbent main body 10 (that is, the front upper end portion 10ea and the back upper end portion 10eb in the pants-shaped state) are respectively joined and fixed to nearest band members 31 and 41. Thus, its appearance is substantially an H shape as viewed from above. From this state, the diaper 1 is two-folded along a folding position which is the predetermined longitudinal position CL1 of the absorbent main body 10 (the longitudinal center position CL1 of the diaper 1). In the band members 31 and 41 facing each other in the foregoing two-folded state, their left-right-direction end portions 31e and 41e are joined by the foregoing side seal portion SS. Consequently, the band members 31 and 41 are connected in an annular shape, forming a pants-shaped diaper 1 in which a waist opening BH and a pair of leg openings LH and LH as shown in FIG. 2.

The absorbent main body 10 in the opened state shown in FIG. 2 has substantially a rectangular shape as viewed from above. the absorbent main body 10 is arranged so that its longitudinal direction extends along the longitudinal direction of the diaper 1. As shown in FIG. 3, the absorbent main body 10 includes: an absorbent body 11; a liquid-permeable top sheet 13 covering the absorbent body 11 from the skin side and serving as the skin-side surface of the absorbent main body 10; and a liquid-impermeable back sheet 15 covering the absorbent body 11 from the non-skin side and serving as the non-skin-side surface of the absorbent main body 10.

The absorbent body 11 includes a liquid-absorbent absorbent core 11*c* and a core-wrapping sheet (not shown) wrapping the outer surface of the absorbent core 11*c*. The absorbent core 11*c* is constituted by liquid-absorbent material (e.g., pulp fiber and super absorbent polymer) formed in a substantially hourglass shape as viewed from above; the substantially hourglass shape is an example of a predetermined shape. As the core-wrapping sheet, a liquid-permeable sheet such as tissue paper or nonwoven fabric can be employed, but core-wrapping sheet is not essential. Further, the shape of the absorbent core 11*c* is not limited to the foregoing substantially hourglass shape as viewed from above, and may be other shape.

The top sheet 13 is a liquid-permeable flexible sheet made of nonwoven fabric or the like. The back sheet 15 is a liquid-impermeable flexible sheet. The back sheet 15 is exemplified by a two-layered, laminated sheet composed of a liquid-impermeable leak-proof sheet (e.g., polyethylene film or polypropylene film) and an exterior sheet made of nonwoven fabric which is attached to the non-skin side of the leak-proof sheet.

As shown in FIG. 2, the back sheet 15 has at least a planar size in which the sheet 15 projects beyond the absorbent body 11 in the longitudinal direction and in the left-right direction. In each of the portions projecting in the left-right direction, a leg gather LG is formed which stretches/contracts in the longitudinal direction. Specifically, in the projecting portions, as elastic members, elastic strings 17 extending along the longitudinal direction are fixed with stretching in the longitudinal direction. Thus, the leg gathers LG having a stretch/contraction ability are formed in the portions.

As shown in FIGS. 2 and 3, for preventing side leakage, the absorbent main body 10 has barrier cuffs LSG and LSG on its end portions in the left-right direction, as leakage-proof walls. Specifically, elastic strings 18 with stretching in the longitudinal direction are attached as elastic members to a sheet portion which is to be the barrier cuff LSG, along the longitudinal direction. Such a configuration is provided on each end portion of the absorbent main body 10 in the left-right direction.

Figure 4:
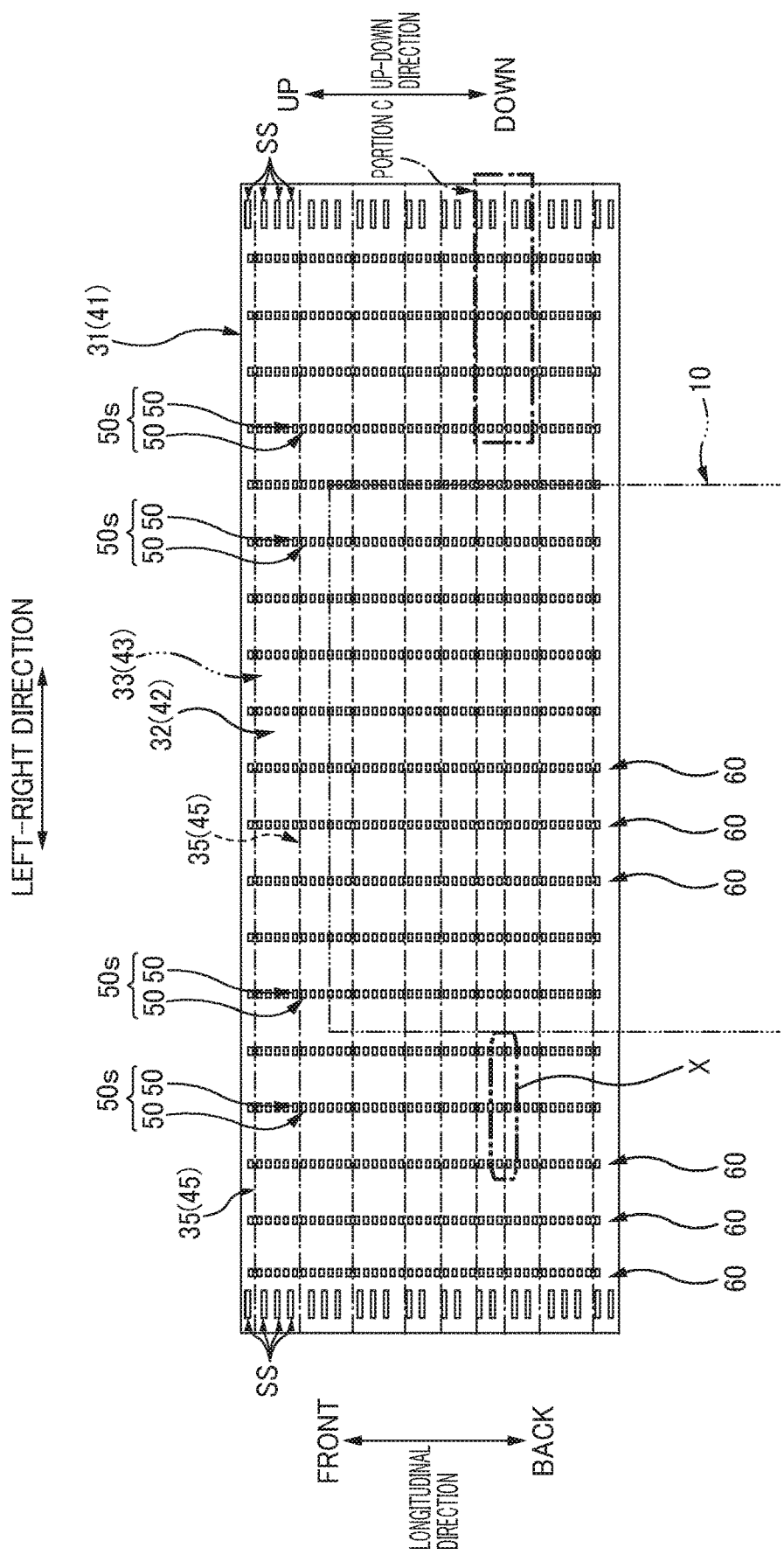
FIG. 4 is a schematic plan view of a front band member 31 which is opened and stretched, as viewed from the non-skin side.

As shown in FIG. 2, the front band member 31 is made of a first sheet 32 and a second sheet 33 which are stacked in the thickness direction and is a sheet member having a substantially rectangular shape as viewed from above. Specifically, as shown in FIG. 3, the first sheet 32 and the second sheet 33 are stacked in the thickness direction, and a pair of surfaces facing each other are joined by a plurality of welded portions 50, 50, . . . (corresponding to the joining portion) arranged discretely in the up-down direction and in the left-right direction as shown in FIG. 4 (to be described later). As shown in FIG. 2, the front band member 31 is arranged projecting beyond the absorbent main body 10 toward the sides in the left-right direction, and the front band member 31 is stacked on and joined to the front-side end portion (the front upper end portion) 10*ea* of the absorbent main body 10 from the non-skin side.

Similar to the front band member 31, the back band member 41 is made of a first sheet 42 and a second sheet 43 which are stacked in the thickness direction and is a sheet-like member having a substantially rectangular shape as viewed from above. Specifically, as shown in FIG. 3, the first sheet 42 and the second sheet 43 are stacked in the thickness direction, and a pair of surfaces facing each other are joined by a plurality of welded portions 50, 50 . . . (corresponding to the joining portion) arranged discretely in the up-down direction (the longitudinal direction) and in the left-right direction in the same manner as the front band member 31 shown in FIG. 4. As shown in FIG. 2, the back band member 41 is arranged projecting beyond the absorbent main body 10 toward the sides in the left-right direction, and the back band member 41 is stacked on and joined to the back-side end portion (the back upper end portion) 10*eb* of the absorbent main body 10 from non-skin side.

In this example, the first sheet 32 (42) and the second sheet 33 (43) for the front band member 31 (the back band member 41) both are made of spun-bonded nonwoven fabric. However, one or more embodiments are not limited thereto. Other types of nonwoven fabric such as SMS (spun-bonded/melt-blown/spun-bonded) nonwoven fabric may be employed. In this example, single fiber made of polypropylene (PP), a typical thermoplastic resin, is used as constituent fiber of nonwoven fabric. However, one or more embodiments are not limited thereto. For example, single fiber made of other thermoplastic resin such as polyethylene (PE) may be used, and composite fiber having a core-sheath structure of PE and PP may be used.

<Front Band Member 31>

A concrete structure of the front band member 31 and the back band member 41, which are stretchable/contractible sheets according to the present embodiment will be described below. As mentioned above, the front band member 31 and the back band member 41 have substantially identical structures. Accordingly, in the following description, concerning things common to both of the front band member 31 and the back band member 41, only those of the front band member 31 will be described as a representative. Concerning the back band member 41, reference signs of its components corresponding to those of the front band member 31 will be indicated by blanketing as necessary, and the concrete description will be omitted.

FIG. 4 is a schematic plan view of the front band member 31 (stretchable/contractible sheet) which is opened and stretched, as viewed from the non-skin side. In FIG. 4, the front band member 31 (41) is shown as a component of the diaper 1, and the band members 31 and 41 can be applied, as a stretchable/contractible sheet, to other than the diaper 1. That is, FIG. 4 is a diagram showing a basic configuration of a stretchable/contractible sheet according to the present embodiment.

As shown in FIG. 4, in the first sheet 32 (42) and the second sheet 33 (43) for the front band member 31 (41), a plurality of elastic members 35, 35, . . . (45, 45, . . . ) such as elastic strings are placed interposing between the pair of surfaces facing each other and aligning with a space in the up-down direction; the elastic members 35 are capable of stretching/contracting in the left-right direction. The elastic members 35 are attached to the sheets 32 and 33 (42 and 43) by the foregoing welded portions 50, 50 . . . . Accordingly, an ability to stretch/contract in the left-right direction is applied to the front band member 31 (41). That is, the welded portions 50, 50, ... have not only a function to join the pair of facing surfaces the first sheet 32 (42) and the second sheet 33 (43), but also has a function to attach the elastic members 35 (45) to the first sheet 32 (42) and the second sheet 33 (43).

In the front band member 31 (41) of the present embodiment, the plurality of welded portions 50, 50, ... are arranged side-by-side in the up-down direction, forming the welded-portion row 60 extending along the up-down direction. A plurality of the welded-portion rows 60 are provided with spaces in the left-right direction. In the example of FIG. 4, each of the welded-portion rows 60 is arranged straight along the up-down direction, but the welded-portion rows 60 may meander in the left-right direction. That is, each of the plurality of welded portions 50 constituting each welded-portion row 60 may be arranged displaced in the left-right direction. Two welded-portion rows 60 and 60 adjacent in the left-right direction are arranged displaced in the up-down direction by a predetermined distance, which is difficult to visually recognize in FIG. 4. That is, two welded portions 50 and 50 adjacent in the left-right direction are located at different positions in the up-down direction (see FIG. 6; to be described later).

As shown in FIG. 4, the plurality of welded portions 50 provided with a predetermined space in the up-down direction and in the left-right direction make it possible to suppress deterioration of touch of the diaper 1 being worn while maintaining the flexibility of the front band member 31 (41). Assuming that a line-shaped welded portion extending lengthwise (continuously) in the up-down direction or in the left-right direction is formed. In a portion where the welded portion is formed, nonwoven fabric becomes hard. And, it is more likely to suppress deformation of nonwoven fabric in a direction in which the line-shaped welded portion extends. In contrast, in the present embodiment, since small welded portions are arranged discretely, it is possible to provide a flexible sheet member which makes it difficult for a user of the diaper 1 (a wearer) to feel curing of nonwoven fabric, and which makes it difficult to suppress deformation of nonwoven fabric in the up-down direction and in the left-right direction. The detail will be described later. Two welded portions 50 and 50 adjacent in the left-right direction are arranged shifting in the up down direction; This makes it possible to suppress displacement of elastic members 35 (45) attached to the front band member 31 (41), and also makes it possible to suppress removal of the elastic members 35 (45) from the band member 31 (41).

In the front band member 31 (41), an elastic member 35 is sandwiched in the up-down direction between two welded portions 50 and 50 adjacent in the up-down direction, among the plurality of welded portions 50 in the welded-portion row 60; and thereby that elastic member 35 is attached to the front band member 31 (41). Specifically, a pair of welded portions 50 and 50 respectively located on both sides of the elastic member 35 in the up-down direction serve as a welded portion pair 50S, and the elastic member 35 is attached by the welded portion pair 50S. FIGS. 5A and 5B are diagrams showing a function to attach an elastic member 35, and are magnified view of the portion C in FIG. 4.

As shown in FIG. 5A, a pair of welded portions 50 and 50 constituting a welded portion pair 50S are placed side-by-side with a space GH50 in the up-down direction. The size of the space GH50 is set to be slightly larger than or equal to the outer diameter D35$t$ (D45$t$) of the elastic member 35 (45) which is stretched at a target stretching ratio in the left-right direction (GH50≧D35$t$); the elastic member 35 (45) is an elastic string, for example. That is, the elastic member 35 in the stretched state is arranged between a welded portion pair 50S in the up-down direction. With such a configuration, in the production processes of the diaper 1 (the front band member 31), after arranging each of elastic members 35 between the first sheet 32 and the second sheet 33 with being stretched, when welding the first sheet 32 and the second sheet 33, it is possible to form the welded portion 50 without overlapping the elastic members 35.

When the elastic member 35 (45) is released from the stretched state, the elastic member 35 (45) enlarges in the up-down direction with contracting in the left-right direction, and its outer diameter D35$t'$ after the enlarging is larger than the space GH50 of the welded portion pair 50S in the up-down direction (D35$t'$>GH50), as shown in FIG. 5B. Accordingly, enlarging of the elastic member 35 (45) in the up-down direction is restricted between the welded portion pair 50S, and thus the elastic member 35 (45) is substantially sandwiched between the welded portions 50 and 50 in the up-down direction. Consequently, the elastic member 35 (45) is attached to the front band member 31 (41). In the pants-shaped diaper 1 of FIG. 1, the elastic members 35 (45) are released from the stretched state. And, in the pants-shaped diaper 1, since the elastic members 35 are joined by the side seal portions SS in both left and right end portions 31$e$ of the front band member 31, the elastic members 35 will not be removed from the front band member 31 even if the front band member 31 (the elastic members 35) are stretched in the left-right direction when putting on the diaper 1.

Meanwhile, the foregoing stretching ratio is a value R indicating how many times longer the entire length L1 of the elastic member 35 (45) the original entire length L0 of the elastic member 35 (45) is (=L1/L0); the entire length L0 is a length in a state in which no force is exerted.

Figure 6:
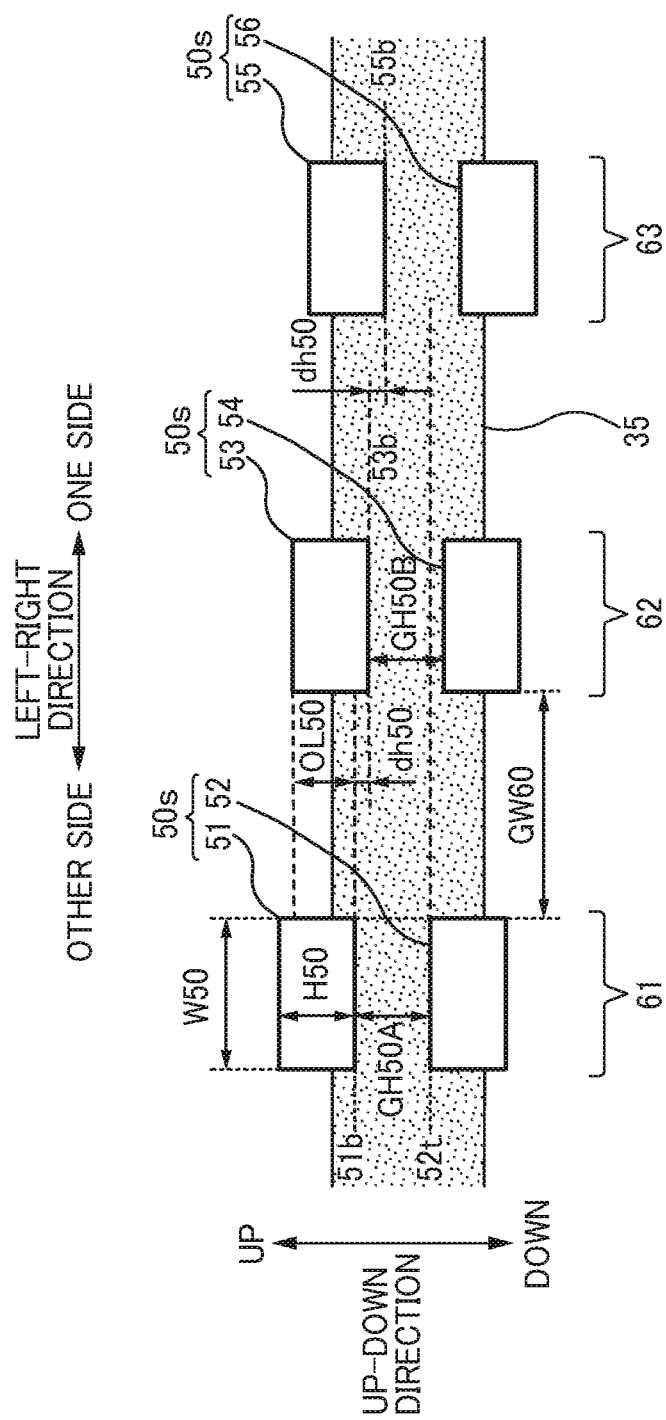
FIG. 6 is a magnified view of the region X of FIG. 4, which is magnified in the natural state, and illustrates arrangement of welded portions 50.

FIG. 6 is a magnified view of the region X of FIG. 4, which is magnified in the natural state, and illustrates arrangement of welded portions 50. Note that the "natural state" is a state in which the diaper 1 or the front band member 31 (41) has been left for a certain period of time. For example, the front band member 31 and the back band member 41 of the diaper 1 are pulled outwardly toward both sides in the left-right direction, making the band members 31 and 41 be "stretched". Then, the stretched state continues for 15 seconds. Thereafter, the diaper 1 is released from being pulled and is placed on a flat surface such as a table. Thus, a state after the diaper 1 has been placed in such a manner in five minutes is defined as a natural state.

FIG. 6 shows a first welded-portion row 61, a second welded-portion row 62 and a third welded-portion row 63; the second welded-portion row 62 is arranged adjacent to the first welded-portion row 61 on the one side (right side in FIG. 6) in the left-right direction, and the third welded-portion row 63 is arranged adjacent to the second welded-portion row 62 on the one side in the left-right direction. The first welded-portion row 61 includes a first welded portion 51 and a second welded portion 52 adjacent to the first welded portion 51 on the lower side in the up-down direction. The first welded portion 51 and the second welded portion 52 forms a welded portion pair 50$s$, and by the welded portion pair 50$s$, an elastic member 35 (45) is sandwiched in the up-down direction and fixed in a similar manner shown in FIG. 5B. Similarly, the second welded-portion row 62 includes a third welded portion 53 and a fourth welded portion 54 adjacent to the third welded portion 53 on the lower side in the up-down direction. The third welded portion 53 and the fourth welded portion 54 forms a welded portion pair 50s. Similarly, the third welded-portion row 63 includes a fifth welded portion 55 and a sixth welded portion 56 adjacent to the fifth welded portion 55 on the lower side in the up-down direction. The fifth welded portion 55 and the sixth welded portion 56 forms a welded portion pair 50s.

The first welded portion 51 and the third welded portion 53 are arranged adjacent to each other in the left-right direction. The first and third welded portions 51 and 53 have portions overlapping in the up-down direction, and the positions of the first and third welded portions 51 and 53 are different in the up-down direction. Specifically, the positions in the up-down direction are different at least between the lower end of the first welded portion 51 (the lowermost end 51b in FIG. 6) and the lower end of the third welded portion 53 (the lowermost end 53b in FIG. 6). In the example of FIG. 6, the first welded portion 51 and the third welded portion 53 overlap in the up-down direction, the length of the overlapping portion in the up-down direction is indicated by a reference symbol OL50. The lowermost end 53b of the third welded portion 53 is arranged at a lower position in the up-down direction than the lowermost end 51b of the first welded portion 51 by a distance dh50. The same positional relation is applied to the third welded portion 53 and the fifth welded portion 55.

Meanwhile, when the front band member 31 (elastic members 35) is stretched in the left-right direction again from the state shown in FIG. 6, the outer diameter D35t gets smaller as stretching the elastic members 35. When the outer diameter D35t becomes smaller than the up-down-direction space GH50 of the welded portion pair 50s, the welded portion pair 50s is released from a state being sandwiched. This allows the elastic members 35 to move in the left-right direction relative to the welded portion pair 50s, and there is a risk of displacement of the elastic members 35. However, in the present embodiment, arranging the first welded portion 51 and the third welded portion 53 in the foregoing positional relation makes it possible to effectively suppress lateral displacement of the elastic members 35.

Figure 7:
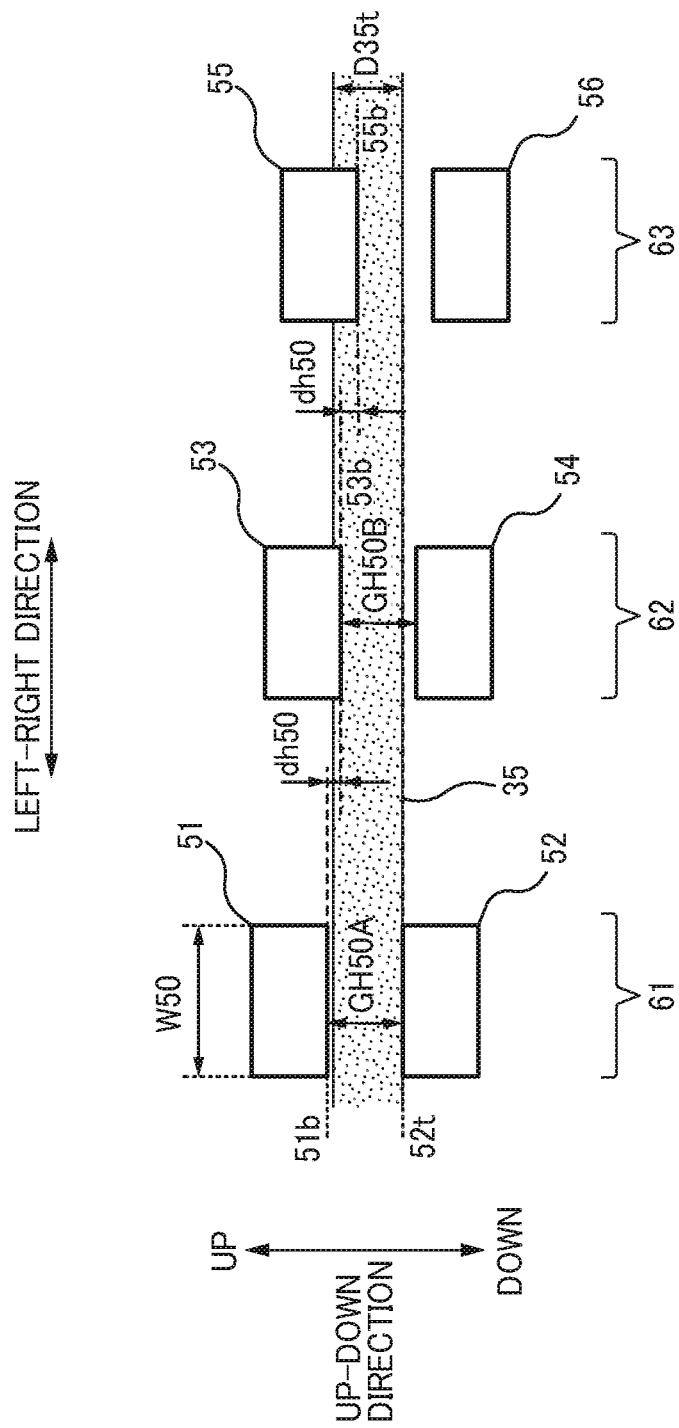
FIG. 7 is a schematic plan view of illustrating a relation between an elastic member 35 and a welded portion pair 50s when a front band member 31 is stretched in the left-right direction from the natural state.

FIG. 7 is a schematic plan view illustrating a relation between the elastic member 35 and the welded portion pair 50s when the front band member 31 is stretched in the left-right direction from the natural state. As mentioned above, in the present embodiment, the lowermost end 53b of the third welded portion 53 is positioned lower than the lowermost end 51b of the first welded portion 51 is. Accordingly, the up-down-direction space GH50A between the lowermost end 51b of the first welded portion 51 and the uppermost end 52t of the second welded portion 52 is larger than the up-down-direction space (GH50A−dh50) between the lowermost end 53b of the third welded portion 53 and the uppermost end 52t of the second welded portion 52. Accordingly, in the stretched state, even if the outer diameter D35t of the elastic member 35 is smaller than the space GH50A, the elastic member 35 is sandwiched between the third welded portion 53 and the second welded portion 52 because the outer diameter D35t is larger than the up-down-direction space (GH50A−dh50) between the lowermost end 53b of the third welded portion 53 and the uppermost end 52t of the second welded portion 52. That is, friction force is exerted on the elastic member 35 by the lowermost end 53b of the third welded portion 53 and the uppermost end 52t of the second welded portion 52, suppressing left-right-direction movement of the elastic member 35.

Further, the up-down-direction space (GH50A−dh50×2) between the lowermost end 55b of the fifth welded portion 55 and the uppermost end 52t of the second welded portion is further smaller than the up-down-direction space (GH50A−dh50) between the lowermost end 53b of the third welded portion 53 and the uppermost end 52t of the second welded portion 52, also suppressing left-right-direction movement of the elastic member 35.

As mentioned above, in the front band member 31 according to the present embodiment, lateral displacement of an elastic member 35 is suppressed even if the outer diameter D35t of the elastic member 35 becomes smaller by being stretched in the left-right direction. Accordingly, when putting on a diaper 1, even if the front band member 31 is stretched in the left-right direction due to a wearer's operation such as pulling the front band member 31 (a waist part of the diaper 1) toward both sides by holding both ends thereof, it is possible to suppress displacement of a position where the elastic member 35 is attached. This can prevent deterioration of fit around the wearer's waist when putting on the diaper 1.

Note that, at the time of putting on the diaper 1, the maximum length of the front band member 31 (the elastic members 35) when pulling it in the left-right direction is about 70% of the maximum length of the elastic members 35 that have been stretched. That is, in a usual use of the diaper 1, there is a possibility that the elastic members 35 are stretched by 70% of the maximum stretchable lengths. Accordingly, in the present embodiment, the up-down-direction space (GH50A−dh50) between the lowermost end 53b of the third welded portion 53 and the uppermost end 52t of the second welded portion 52 is designed so that the space (GH50A−dh50) is smaller than the outer diameter D35t (70%) of the elastic member 35 in which the elastic member 35 has been stretched to 70% of the maximum (D35t (70%)>(GH50A−dh50)). Accordingly, in a usual use of the diaper 1, the outer diameter D35t of the elastic member 35 is larger than the up-down-direction space (GH50−dh50) between the lowermost end 53b of the third welded portion 53 and the uppermost end 52t of the second welded portion 52. This makes it easier for the third welded portion 53 and the second welded portion 52 to more reliably suppress lateral displacement of the elastic member 35.

In the front band member 31 (41), the up-down-direction displacement of two welded portions 50 and 50 adjacent in the left-right direction is restricted to a predetermined range. Specifically, the first welded portion 51 and the third welded portion 53 are arranged so that the up-down-direction displacement dh50 between the lowermost end 51b of the first welded portion 51 and the lowermost end 53b of the third welded portion 53 is smaller than the length OL50 of the portion where the first welded portion 51 and the third welded portion 53 overlap in the up-down direction. If the up-down-direction displacement between the two welded portions 50 is excessively large, there is a possibility that, according to the displacement, the elastic member 35 is attached inclined with respect to the left-right direction. For example, in FIG. 6, in the case where the displacement dh50 is larger than the length OL50, the elastic member 35 is attached inclined downward in the up-down direction and extending from the other side to the one side in the left-right direction. In this case, stretching/contracting force of the elastic member 35 is exerted in the up-down direction, and this worsens a function to stretch/contract the front band member 31 in the left-right direction. In addition, the up-down-direction contraction of the front band member 31 causes a risk of deterioration of fit in the waist region of the diaper 1 and a risk of deterioration of touch due to unnecessary creases. Accordingly, in the present embodiment, displacement dh50<length OL50, and this suppresses arranging the elastic member 35 with being inclined.

The up-down-direction displacement dh50 between the lowermost end 51b of the first welded portion 51 and the lowermost end 53b of the third welded portion 53 is smaller than the outer diameter D35t (100%) of the elastic member 35 which is stretched at 100% (at a maximum stretching ratio). If the first welded portion 51 and the third welded portion 53 are placed displaced in the up-down direction as mentioned above, when attempting to arrange the elastic member 35 along the left-right direction, that elastic member 35 sometimes inclines in the up-down direction. In the case where the displacement dh50 is larger than the outer diameter D35t of the elastic member 35 (100%), this makes relatively large the inclination of the elastic member 35 in the up-down direction, and there is a risk that the elastic member 35 curves or meanders. In this case, a function to stretch/contract the front band member 31 in the left-right direction deteriorates. Accordingly, in the present embodiment, the arrangement of the welded portions 50 is adjusted so that dh50<D35t (100%).

The shape of each welded portion 50 is a laterally elongated rectangle, as shown in FIG. 6, in which the length W50 in the left-right direction is larger than the length H50 in the up-down direction (W50>H50). In the present embodiment, in the natural state, the elastic member 35 is attached to the front band member 31 (41) by being sandwiched in the up-down direction between the welded portions 50. Accordingly, making the welded portion 50 have a laterally-elongated shape increases the area (length) in which the elastic member 35 and the welded portion 50 are in contact with each other in the left-right direction. By this increase, friction force in the left-right direction increases, making it easier to fix the elastic member 35. This makes it easier to further suppress the left-right-direction displacement of the elastic members 35.

In the example of FIG. 6, all the welded portions 51 to 56 have an identical shape, but each welded portion may have a different shape. For example, the following shape is acceptable: the uppermost ends of the first welded portion 51 and the third welded portion 53 are located at the same position, and the lower-end positions are located at different positions. That is, the up-down-direction length of the first welded portion 51 may be larger than that of the third welded portion 53.

Figure 8A:
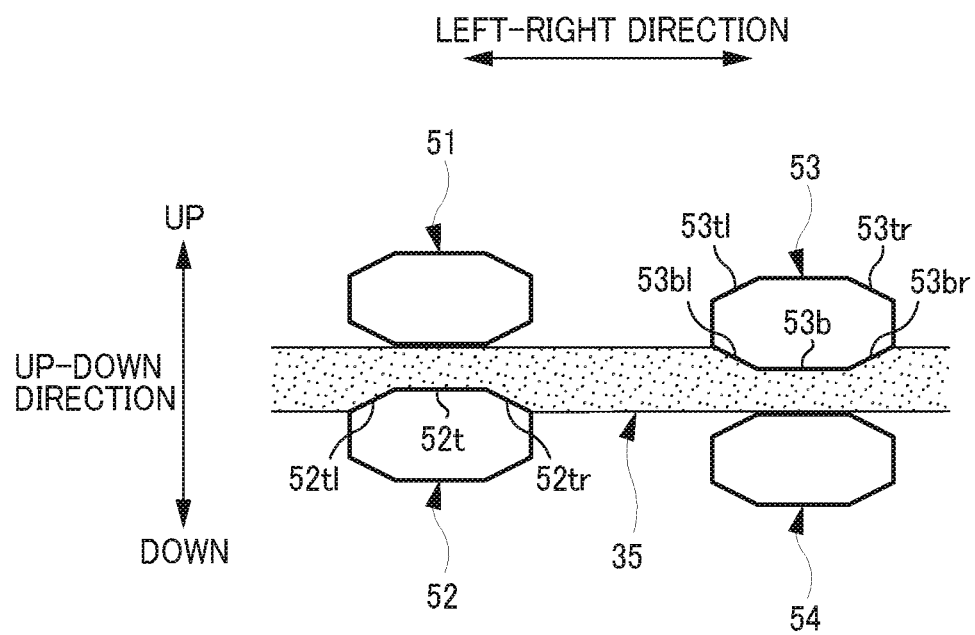
FIGS. 8A and 8B are diagrams illustrating modified examples of the shape of the welded portion 50.
Figure 8B:
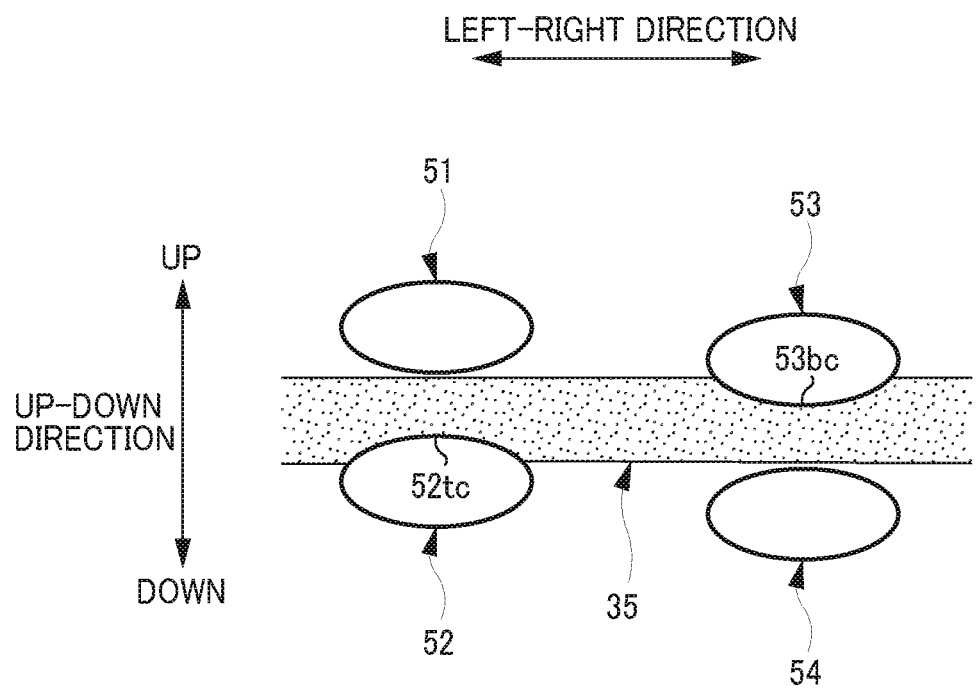

Instead of a rectangle shown in FIG. 6, each welded portion 50 may have other shape such as a polygon or an ellipse. FIGS. 8A and 8B are diagrams illustrating modified examples of the shape of the welded portion 50. FIG. 8A shows a welded portion 50 having a substantially octagonal shape in which four corners of a rectangular welded portion 50 are cut out. For example, the third welded portion 53 has a cut-out 53b1 in the lower left corner, a cut-out 53br in the lower right corner, a cut-out 53tl in the upper left corner, and a cut-out 53tr in the upper right corner.

In the stretched state shown in FIG. 7, it is described that the elastic member 35 is sandwiched between the uppermost end 52t of the second welded portion 52 and the lowermost end 53b of the third welded portion 53. In the case where the third welded portion 53 has laterally-elongated rectangular shape, the bottom side of the rectangle of the third welded portion 53 is the lowermost end 53b. That is, though friction force is produced by contact of the elastic member 35 with the entire bottom side of the third welded portion 53, it is possible to suppress left-right-direction displacement of the elastic member 35 due to that friction force. On the other hand, in the case where the third welded portion 53 has a cut-out shown in FIG. 8A, the elastic member 35 is in contact with the cut-out 53b1 and the cut-out 53br of the third welded portion 53 and the bottom side of the third welded portion 53 including the lowermost end 53b. In this case, the cut-outs 53b1 and 53br make longer the length along which the elastic member 35 is in contact with the third welded portion 53. This produces greater friction force, making it easier to suppress displacement of the elastic member 35. Thus, changing the shape of the welded portion 50 changes the length (the area) of a portion where the elastic member 35 and the welded portion 50 in contact with each other, making it possible to adjust the magnitude of the friction force. Note that, the cut-outs 53b1 and 53br may be formed in a curved shape, not in a straight shape shown in FIG. 8A.

FIG. 8B shows a case where the welded portion 50 has laterally-elongated, elliptical shape. In FIG. 8B, in the natural state, the elastic member 35 is in contact with the third welded portion 53 along a lower curved line 53bc including the lowermost end 53b. Similarly, the elastic member 35 is in contact with the second welded portion 52 along an upper curved line 52tc including the uppermost end 52t. Compared to the case of contact only with the bottom side of a rectangle, this makes longer the length along which the elastic member 35 is in contact with the third welded portion 53 (the second welded portion 52). Accordingly, a larger friction force is produced, making it easier to suppress the displacement of the elastic member 35. The term "elliptical" includes a so-called oval shape such as an elongated circle. The shape of the welded portion 50 is not limited to the examples of FIGS. 8A and 8B, and other shape may be employed.

As mentioned above, each of the welded portions 50 may have different shape, but in the following description, all the welded portions 50 are formed in an identical shape shown in FIG. 6, for the purpose of explanation. Note that, in the production processes of the diaper 1 (the front band member 31), the welded portions 50 are formed by commonly-known means such as an ultrasonic welding device or a heat-sealing device. In the case where an ultrasonic welding device (not shown) are used as an concrete example of a method for manufacturing the front band member 31, the welded portion 50 is formed as follow: the continuous members of the first sheet 32 and the second sheet 33 (including the elastic members 35) are transported in the direction of rotation of the anvil roll while being wrapped around the outer circumferential surface of the anvil roll; an ultrasonic horn is arranged facing the outer circumferential surface of the anvil roll; and the ultrasonic horn applies to the continuous members ultrasonic vibration in the thickness direction of the first and second sheets 32 and 33. On the outer circumferential surface of the anvil roll, a plurality of convex portions are formed projecting, and therefore the welded portions 50 are formed according to the shapes and arrangement of the convex portions. Accordingly, if all the welded portions 50 have the same shape, all the convex portions on the outer circumferential surface of the anvil roll can have the same shape. This makes the convex portions difficult to wear and makes easier inspections and maintenance, and therefore it is possible to reduce production cost.

In the front band member 31 (41) according to the present embodiment, the outer diameter D35t (100%) of the elastic member 35 in which the elastic member 35 has been stretched to 100% (stretched at maximum) is smaller than the up-down-direction space GH50A between the first welded portion 51 and the second welded portion 52. Similarly, the outer diameter D35t (100%) of the elastic member 35 in which the elastic member 35 has been stretched to 100% (stretched at maximum) is smaller than the up-down-direction space GH50B between the third welded portion 53 and the fourth welded portion 54. With such a configuration, it is easy to arrange the elastic member 35 in the up-down-direction space GH50A and in the up-down-direction space GH50B, which are each between a welded portion pair 50s. In other words, it is possible to arrange the elastic members 35 without overlapping a pair of welded portions 50 and 50 which are adjacent in the up-down direction. As mentioned above, in the production processes of the front band member 31, ultrasonic vibration is applied and is welded in a portion of the band member 31 which overlaps a convex portion of the anvil roll (that is, a region in which the welded portion 50 is formed). Accordingly, in the case where the elastic member 35 overlaps the convex portion the anvil roll (the welded portion 50), there is a risk that the elastic member 35 undergoes ultrasonic vibration and is cut. On the contrary, in the case where the relations that diameter D35t (100%)<space GH50A and that diameter D35t (100%)<space GH50B are satisfied, the elastic member 35 in the stretched state is easy to be arranged between convex portions on the outer circumferential surface of the anvil roll, in the production processes. This makes it easier to suppress cut of the elastic member 35 by ultrasonic vibration.

Further, the outer diameter D35t (100%) of the elastic member 35 in which the elastic member 35 has been stretched to 100% (stretched at maximum) is smaller than the up-down-direction space (GH50A−dh50) between the second welded portion 52 and the third welded portion 53. As shown in FIG. 6, the up-down-direction space (GH50A−dh50) between the second welded portion 52 and the third welded portion 53 is smaller than the space GH50A between the first welded portion 51 and the second welded portion 52. Since the outer diameter D35t (100%) of elastic member 35 is smaller than the smaller space (GH50A−dh50), it is possible to further reduce a risk that the elastic member 35 is cut by ultrasonic vibration.

Furthermore, the outer diameter D35t (100%) of the elastic member 35 in which the elastic member 35 has been stretched to 100% (stretched at maximum) is smaller than the up-down-direction space (GH50A−dh50×2) between the second welded portion 52 and the fifth welded portion 55. The up-down-direction space (GH50A−dh50×2) between the fifth welded portion 55 and the second welded portion 52 is further smaller than the space (GH50A−dh50) between the third welded portion 53 and the second welded portion 52. Since the outer diameter D35t (100%) of the elastic member 35 is smaller than the smaller space (GH50A−dh50×2), it is possible to further reduce a risk that the elastic member 35 is cut by ultrasonic vibration.

The up-down-direction space GH50A between the first welded portion 51 and the second welded portion 52 is equal to the up-down-direction space GH50B between the third welded portion 53 and the fourth welded portion 54. If each welded portion 50 has the same shape and all up-down-direction space are equal, the welded portions 50 are uniformly formed in the welded-portion rows 61 and 62. Forming uniformly the welded portions 50 suppresses breakage of a portion of the front band member 31 having a locally small strength of joining the first sheet 32 and the second sheet 33, and also suppresses deterioration of touch of a portion having locally large strength of joining.

Further, a space GW60 between two welded-portion rows 60 and 60 adjacent in the left-right direction (in FIG. 6, the left-right-direction distance between the second welded portion 52 and the third welded portion 53) may be less than or equal to 6 mm. If the space GW60 is excessively large, it weakens a force for sandwiching up and down the elastic member 35 between the uppermost end 52t of the second welded portion 52 and the lowermost end 53b of the third welded portion 53. Consequently, sufficient friction force does not produce and there is a risk that displacement of the elastic member 35 is produced. On the contrary, if the space GW60 is at least less than or equal to 6 mm, this makes it possible to produce effective friction force between the elastic member 35 and the second and third welded portions 52 and 53 in the natural state. This makes it easier to suppress left-right-direction displacement of the elastic member 35.

As mentioned above, good fit of a diaper 1 (an absorbent article) can be realized by using, as its waist member, the front band member 31 (41) having the foregoing characteristics. Specifically, stretching/contracting force caused by the elastic member 35 (45) is exerted uniformly on the entirety of the front band member 31 (41), and this makes it difficult for displacement of the elastic member 35 (45) to occur even when the front band member 31 (41) is stretched at the time of putting on the diaper 1. This makes it easier to suppress local concentration of stretching/contracting force which is caused by the elastic member 35 (45), and also makes it easier to suppress deterioration of exertion of the stretching/contracting force. This makes it easier to keep good fit around the waist part of a wearer.

The pitch of the elastic members 35 of the front band member 31 in the up-down direction is different from the pitch of the elastic members 45 of the back band member 41 in the up-down direction. If the pitches in the up-down direction are different between the elastic members 35 and the elastic members 45, contraction force exerted by the elastic members on unit area becomes different between the front band member 31 and the back band member 41. Accordingly, the size and the shape of creases formed at a time of contract can be different between the front side and the back side of the diaper 1. Since the size and the shape of creases formed on each surface are different, the front band member 31 and the back band member 41 are less likely to be in close contact in the thickness direction, making it easier to handle the diaper 1. For example, at the time of shipping the diaper 1 from its manufacturing plant, the front band member 31 and the back band member 41 are compressed and packed with being stacked in the thickness direction. When a user (purchaser) uses the diaper 1, he or she has to open the front band member 31 and the back band member 41 in the front-back direction to form its waist opening (see FIG. 1). At this occasion, the user is easy to open the waist opening because the front band member 31 and the back band member 41 are not in close contact with each other.

The pitch of the elastic members 45 of the back band member 41 in the up-down direction is larger than the pitch of the elastic members 35 of the front band member 31 in the up-down direction. The wider the pitch between elastic members in the up-down direction is, the larger creases formed in the band members 31 and 41 at the time of contracting the elastic members 35, 45 are. At this occasion, large creases are more likely to be formed in the back band member 41. Accordingly, in the region of buttocks whose movement is large, large creases are formed in the back band member 41, making it easier for the back band member 41 to stretch following the wearer's body (buttocks) movement. This makes it easier to suppress deterioration of fit.

While embodiments are described above, the above-mentioned embodiments are provided for facilitating the understanding, and are not to be interpreted as limiting the present invention. As a matter of course, the present invention can be altered and improved without departing from the gist thereof and the present invention includes equivalent thereof. For example, the invention can be altered as described below.

In the foregoing embodiment, it is not necessary that the side seal portions SS are rectangular. Not only a rectangle, but also any type of shape such as an oval, a circle, and a parallelogram may be employed. In addition, it is not necessary that the side seal portions SS are composed of a plurality of side welded portions SS arranged with spacing in the up-down direction. For example, a side seal portion SS extending from the upper end to the lower end may be provided on each of the end portions of the diaper 1 in the left-right direction.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

1 diaper (absorbent article, disposable diaper),
10 absorbent main body, 10ea end portion, 10eb end portion,
11 absorbent body, 11c absorbent core,
13 top sheet, 15 back sheet,
17 elastic string, 18 elastic string,
31 front band member, 31e end portion,
32 first sheet, 33 second sheet,
35 elastic member,
41 back band member, 41e end portion,
42 first sheet, 43 second sheet,
45 elastic member,
50 welded portion, 50s welded portion pair,
51 first welded portion, 52 second welded portion, 53 third welded portion,
54 fourth welded portion,
55 fifth welded portion, 56 sixth welded portion,
60 welded-portion row,
61 first welded-portion row, 62 second welded-portion row, 63 third welded-portion row,
BH waist opening, LH leg opening,
CL1 center position,
LG leg gather,
LSG barrier cuff (leakage-proof wall),
SS side seal portion

What is claimed is:

1. An absorbent article having an up-down direction and a left-right direction intersecting each other, comprising:
an absorbent main body that absorbs excrement;
a front band member disposed along the left-right direction and joined to a front-upper-end portion of the absorbent main body; and
a back band member disposed along the left-right direction separately from the front band member, and joined to a back-upper-end portion of the absorbent main body, wherein
the front band member and the back band member each comprise:
a first sheet;
a second sheet;
a plurality of welded portions that joins the first sheet and the second sheet; and
a plurality of elastic members that is stretchable and contractible in the left-right direction,
the plurality of elastic members is arranged with a space in the up-down direction and between the first sheet and the second sheet,
the plurality of welded portions comprises, above a certain elastic member of the plurality of the elastic members:
a first welded portion; and
a third welded portion adjacent to the first welded portion on a one side in the left-right direction,
the plurality of welded portions further comprises, below the certain elastic member:
a second welded portion; and
a fourth welded portion adjacent to the second welded portion on the one side,
the certain elastic member is attached to the first sheet and the second sheet,
the certain elastic member is sandwiched in the up-down direction between the first welded portion and the second welded portion while the certain elastic member is contracting in the left-right direction,
the certain elastic member is sandwiched in the up-down direction between the third welded portion and the fourth welded portion while the certain elastic member is contracting in the left-right direction,
the first welded portion and the third welded portion have portions that overlap in the up-down direction,
a position of a lower end of the first welded portion is different in the up-down direction from a position of a lower end of the third welded portion, and
a length of a portion where the first welded portion and the third welded portion overlap in the up-down direction is larger than a length in the up-down direction between a lowermost end of the first welded portion and a lowermost end of the third welded portion,
an end portion of the front band member in the left-right direction is joined to an end portion of the back band member in the left-right direction by a first side seal portion,
another end portion of the front band member in the left-right direction is joined to another end portion of the back band member in the left-right direction by a second side seal portion,
the first welded portion is located between the first side seal portion and the second side seal portion in the left-right direction,
the second welded portion is located between the first side seal portion and the second side seal portion in the left-right direction, and
the third welded portion is located between the first side seal portion and the second side seal portion in the left-right direction.

2. The absorbent article according to claim 1, wherein a length of the first welded portion in the left-right direction is larger than a length of the first welded portion in the up-down direction.

3. The absorbent article according to claim 1, wherein the second welded portion and the third welded portion have a shape in which four corners of a rectangle are cut out.

4. The absorbent article according to claim 1, wherein the second welded portion and the third welded portion have an elliptical shape.

5. The absorbent article according to claim 1, wherein the first to the fourth welded portions have an identical shape.

6. The absorbent article according to claim 1, wherein
an outer diameter of the elastic member when the elastic member is stretched to a maximum stretchable length in the left-right direction is smaller than a length in the up-down direction between a lowermost end of the first welded portion and an uppermost end of the second welded portion, and
the outer diameter of the elastic member when the elastic member is stretched to the maximum stretchable length in the left-right direction is smaller than a length in the up-down direction between a lowermost end of the third welded portion and an uppermost end of the fourth welded portion.

7. The absorbent article according to claim 1, wherein an outer diameter of the elastic member when the elastic member is stretched to a maximum stretchable length in the left-right direction is smaller than a length in the up-down direction between a lowermost end of the third welded portion and an uppermost end of the second welded portion.

8. The absorbent article according to claim 1, wherein
the plurality of welded portions comprises, above the certain elastic member, a fifth welded portion adjacent to the third welded portion on the one side, and
an outer diameter of the elastic member when the elastic member is stretched to a maximum stretchable length in the left-right direction is smaller than a length in the up-down direction between a lowermost end of the fifth welded portion and an uppermost end of the second welded portion.

9. The absorbent article according to claim 1, wherein a length in the up-down direction between a lowermost end of the first welded portion and an uppermost end of the second welded portion is equal to a length in the up-down direction between a lowermost end of the third welded portion and an uppermost end of the fourth welded portion.

10. The absorbent article according to claim 1, wherein an outer diameter of the elastic member when the elastic member is stretched to 70% of a maximum stretchable length in the left-right direction is larger than a length in the up-down direction between a lowermost end of the third welded portion and an uppermost end of the second welded portion.

11. The absorbent article according to claim 1, wherein in the left-right direction, a space of two adjacent welded portions is less than or equal to 6 mm.

12. The absorbent article according to claim 1, wherein in the up-down direction, a space of the elastic members disposed in the front band member is different from a space of the elastic members disposed in the back band member.

13. The absorbent article according to claim 12, wherein in the up-down direction, a space of the elastic members disposed in the front band member is smaller than a space of the elastic members disposed in the back band member.

14. The absorbent article according to claim 1, wherein in the up-down direction, a space of the elastic members disposed in the front band member is different from a space of the elastic members disposed in the back band member.

15. An absorbent article having an up-down direction and a left-right direction intersecting each other, comprising:
an absorbent main body that absorbs excrement;
a front band member disposed along the left-right direction and joined to a front-upper-end portion of the absorbent main body; and
a back band member disposed along the left-right direction separately from the front band member, and joined to a back-upper-end portion of the absorbent main body, wherein the front band member and the back band member each comprise:
a first sheet;
a second sheet;
a plurality of welded portions that joins the first sheet and the second sheet; and
a plurality of elastic members that is stretchable and contractible in the left-right direction,
the plurality of elastic members is arranged with a space in the up-down direction and between the first sheet and the second sheet,
the plurality of welded portions comprises, above a certain elastic member of the plurality of the elastic members:
a first welded portion; and
a third welded portion adjacent to the first welded portion on a one side in the left-right direction,
the plurality of welded portions further comprises, below the certain elastic member:
a second welded portion; and
a fourth welded portion adjacent to the second welded portion on the one side,
the certain elastic member is attached to the first sheet and the second sheet,
the certain elastic member is sandwiched in the up-down direction between the first welded portion and the second welded portion while the certain elastic member is contracting in the left-right direction,
the certain elastic member is sandwiched in the up-down direction between the third welded portion and the fourth welded portion while the certain elastic member is contracting in the left-right direction,
the first welded portion and the third welded portion have portions overlapping in the up-down direction,
a position of a lower end of the first welded portion is different in the up-down direction from a position of a lower end of the third welded portion, and
an outer diameter of the elastic member when the elastic member is stretched to a maximum stretchable length in the left-right direction is larger than a length in the up-down direction between a lowermost end of the first welded portion and a lowermost end of the third welded portion,
an end portion of the front band member in the left-right direction is joined to an end portion of the back band member in the left-right direction by a first side seal portion,
another end portion of the front band member in the left-right direction is joined to another end portion of the back band member in the left-right direction by a second side seal portion,
the first welded portion is located between the first side seal portion and the second side seal portion in the left-right direction,
the second welded portion is located between the first side seal portion and the second side seal portion in the left-right direction, and
the third welded portion is located between the first side seal portion and the second side seal portion in the left-right direction.

16. The absorbent article according to claim 15, wherein a length of the first welded portion in the left-right direction is larger than a length of the first welded portion in the up-down direction.

17. The absorbent article according to claim 15, wherein the second welded portion and the third welded portion have a shape in which four corners of a rectangle are cut out.

18. The absorbent article according to claim 15, wherein the second welded portion and the third welded portion have an elliptical shape.

* * * * *